(12) United States Patent
Seifert et al.

(10) Patent No.: US 8,612,021 B2
(45) Date of Patent: Dec. 17, 2013

(54) MAGNETIC RESONANCE IMAGING COMPATIBLE MEDICAL ELECTRICAL LEAD AND METHOD OF MAKING THE SAME

(75) Inventors: Kevin R. Seifert, Forest Lake, MN (US); Mark T. Marshall, Forest Lake, MN (US); Mariya Lazebnik, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/324,406

(22) Filed: Dec. 13, 2011

(65) Prior Publication Data
US 2012/0209365 A1 Aug. 16, 2012

Related U.S. Application Data

(60) Provisional application No. 61/441,537, filed on Feb. 10, 2011.

(51) Int. Cl.
*A61N 1/05* (2006.01)

(52) U.S. Cl.
USPC .............................. 607/116; 29/600; 29/601

(58) Field of Classification Search
USPC ........................................................ 607/116
See application file for complete search history.

(56) References Cited

U.S. PATENT DOCUMENTS

| | | | |
|---|---|---|---|
| 5,015,800 A * | 5/1991 | Vaupotic et al. | 174/34 |
| 5,197,468 A | 3/1993 | Proctor et al. | |
| 5,283,390 A | 2/1994 | Hubis et al. | |
| 6,643,552 B2 * | 11/2003 | Edell et al. | 607/116 |
| 7,013,180 B2 | 3/2006 | Villaseca et al. | |
| 7,304,277 B2 | 12/2007 | Weber | |
| 7,363,090 B2 | 4/2008 | Halperin et al. | |
| 7,423,496 B2 | 9/2008 | Scheuermann | |
| 7,561,906 B2 | 7/2009 | Atalar et al. | |
| 7,702,387 B2 | 4/2010 | Stevenson et al. | |
| 2003/0050557 A1 | 3/2003 | Susil et al. | |

(Continued)

FOREIGN PATENT DOCUMENTS

| EP | 1 545 159 A1 | 6/2005 |
|---|---|---|
| WO | 2009/039427 A2 | 3/2009 |

OTHER PUBLICATIONS (PCT/US2012/020159) PCT Notification of Transmittal of the International Search Report and the Written Opinion of the International Searching Authority, 12 pages.

*Primary Examiner* — Christopher D Koharski
*Assistant Examiner* — Michael Carey
(74) *Attorney, Agent, or Firm* — Stephen W. Bauer; Michael J. Ostrom

(57) ABSTRACT

This disclosure describes an implantable medical lead, and method of making such a lead or components of the lead, that reduces the undesirable effects the fields generated by an MRI device may have on the implantable medical lead and the implantable medical device. The implantable medical lead includes an RF filter placed in series with an electrical path to an electrode of the lead. In one example, the RF filter may comprise a conductor wound in such a manner that it provides an inductance and capacitance that provides the RF filter with a resonant frequency, and in some instances, multiple resonant frequencies. At frequencies around the resonant frequency of the RF filter, the RF filter presents a high impedance, thereby blocking the signal from or at least attenuating the signal propagating to the electrode. At frequencies far from the resonant frequency, the RF filter presents a low impedance.

28 Claims, 9 Drawing Sheets

(56) References Cited

U.S. PATENT DOCUMENTS

| | | |
|---|---|---|
| 2003/0179536 A1 | 9/2003 | Stevenson et al. |
| 2005/0109841 A1 | 5/2005 | Ryan et al. |
| 2005/0165301 A1 | 7/2005 | Smith et al. |
| 2006/0025820 A1 | 2/2006 | Phillips et al. |
| 2007/0047061 A1 | 3/2007 | Kowarz |
| 2007/0168006 A1 | 7/2007 | Gray |
| 2008/0039709 A1 | 2/2008 | Karmarkar |
| 2008/0154348 A1 | 6/2008 | Atalar et al. |
| 2008/0243218 A1 | 10/2008 | Bottomley et al. |
| 2008/0262584 A1 | 10/2008 | Bottomley et al. |
| 2009/0076579 A1* | 3/2009 | Boser et al. .......... 607/122 |
| 2009/0149933 A1 | 6/2009 | Ameri |
| 2009/0171421 A1 | 7/2009 | Atalar et al. |
| 2009/0179716 A1 | 7/2009 | Gay |
| 2009/0204171 A1 | 8/2009 | Ameri |
| 2009/0204183 A1 | 8/2009 | Kreidler et al. |
| 2009/0243756 A1 | 10/2009 | Stevenson et al. |
| 2009/0281592 A1 | 11/2009 | Vase |
| 2010/0138192 A1 | 6/2010 | Min |
| 2010/0331940 A1 | 12/2010 | Indravudh et al. |
| 2010/0331942 A1 | 12/2010 | Cholette et al. |

* cited by examiner

MAGNETIC RESONANCE IMAGING COMPATIBLE MEDICAL ELECTRICAL LEAD AND METHOD OF MAKING THE SAME

This application claims the benefit of U.S. Provisional Application No. 61/441,537, filed on Feb. 10, 2011, the content of which is incorporated herein by reference in its entirety.

TECHNICAL FIELD

The present disclosure relates to implantable medical leads and methods of manufacturing such leads or components of such leads.

BACKGROUND

Implantable leads are used with a wide variety of medical devices to form medical systems for delivering therapy to a patient or sensing physiological parameters of the patient. For example, implantable leads are commonly connected to implantable pacemakers, defibrillators, cardioverters, or the like, to form an implantable cardiac system that provides electrical stimulation to the heart or sensing of electrical activity of the heart. The electrical stimulation pulses can be delivered to the heart and the sensed electrical signals can be sensed by electrodes disposed on the leads, e.g., typically near distal ends of the leads. In that case, the leads may be implanted such that the electrodes are positioned with respect to various cardiac locations so that the cardiac device can deliver pulses to or sense activity of the appropriate locations. Implantable leads are also used in neurological devices, muscular stimulation therapy, gastric system stimulators and other implantable medical devices (IMDs).

Occasionally, patients that have implantable leads may benefit, or even require, various medical imaging procedures to obtain images of internal structures of the patient. One common medical imaging procedure is magnetic resonance imaging (MRI). MRI procedures may generate higher resolution and/or better contrast images (particularly of soft tissues) than other medical imaging techniques. MRI procedures also generate these images without delivering ionizing radiation to the body of the patient, and, as a result, MRI procedures may be repeated without exposing the patient to such radiation.

During an MRI, the patient or a particular part of the patient's body is positioned within an MRI device. The MRI device generates a variety of magnetic and electromagnetic fields to obtain the images of the patient, including a static magnetic field, gradient magnetic fields, and radio frequency (RF) fields. The static MRI field may be generated by a primary magnet within the MRI device and may be present prior to initiation of the MRI procedure. The gradient magnetic fields may be generated by electromagnets of the MRI device and may be present during the MRI procedure. The RF magnetic field may be generated by transmitting/receiving coils of the MRI device and may be present during the MRI procedure. If the patient undergoing the MRI procedure has an implantable medical system, the various fields produced by the MRI device may have undesirable effects on the medical leads or the medical device to which the leads are coupled. For example, the gradient magnetic fields or the RF fields generated during the MRI procedure may induce energy on the implantable leads (e.g., in the form of a current), which may be conducted to tissue proximate to the electrode and cause a rise in temperature of the tissue.

SUMMARY

This disclosure describes an implantable medical lead, and method of making such a lead or components of the lead, that reduces the undesirable effects the fields generated by an MRI device may have on the implantable medical lead and the implantable medical device. The implantable medical lead includes an RF filter placed in series with an electrical path to an electrode of the lead. In one example, the RF filter may comprise a conductor wound in such a manner that it provides an inductance and capacitance that provides the RF filter with a resonant frequency, and in some instances, multiple resonant frequencies. At frequencies around the resonant frequency of the RF filter, the RF filter presents a high impedance, thereby blocking the signal from or at least attenuating the signal propagating to the electrode. At frequencies far from the resonant frequency, the RF filter presents a low impedance. By designing the RF filter to have a resonant frequency around the frequency of MRI device, energy induced on leads by the MRI device may be significantly reduced while allowing energy associated with therapies to pass substantially unaffected.

In one example, this disclosure describes a method that includes obtaining an electrical conductor having a conductive core, a first insulation layer surrounding the conductive core, and a second insulation layer surrounding the first insulation layer. The second insulation layer has a thermal property that occurs at a lower temperature than the same thermal property of the first insulation layer. The method also includes winding the electrical conductor to form an RF filter and heating at least a portion of the RF filter to a temperature at or above the thermal property of the second insulation layer and below the thermal property of the first insulation layer such that the second insulation layers of adjacent windings of the electrical conductor bond throughout at least the portion of the RF filter.

Although described mainly in the context of MRI procedures, the implantable medical leads of this disclosure may also allow the patient to undergo other medical procedures that utilize high frequency signals that may affect operation of the medical electrical lead, such as electrocautery procedures, diathermy procedures, ablation procedures, electrical therapy procedures, magnetic therapy procedures, or the like. Moreover, the implantable medical leads described in this disclosure may also reduce the effects of high frequency signals encountered in medical and non-medical environments, such in an environment with RFID reading devices including surgeries that utilize RFID tagged instruments, towels, or the like.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
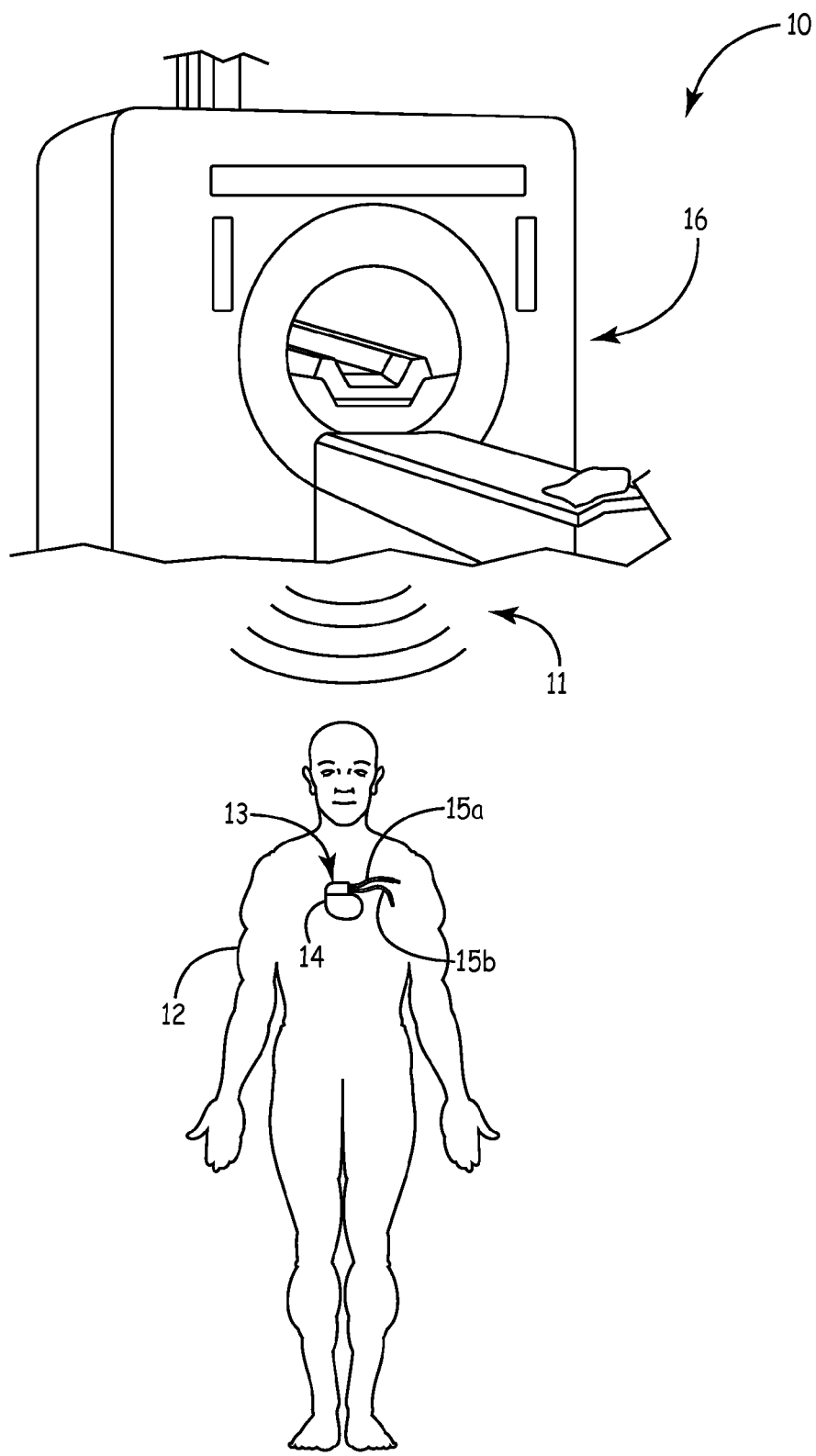
FIG. 1 is a conceptual diagram illustrating an environment in which an implantable medical system is in an environment having an MRI device.

FIG. 1 is a conceptual diagram illustrating an environment 10 in which an implantable medical system 13 is exposed to external fields 11. In the example illustrated in FIG. 1, environment 10 includes an MRI device 16 that generates external fields 11. MRI device 16 generates magnetic and RF fields to produce images of body structures for diagnosing injuries, diseases and/or disorders. In particular, MRI device 16 generates a static magnetic field, gradient magnetic fields and RF fields as is well know in the art. The static magnetic field is a non time-varying magnetic field that is typically always present around MRI device 16 whether or not an MRI procedure is in progress. Gradient magnetic fields are pulsed magnetic fields that are typically only present while the MRI procedure is in progress. RF fields are pulsed high frequency fields that are also typically only present while the MRI procedure is in progress. The magnitude, frequency or other characteristic of the static magnetic field, gradient magnetic fields and RF fields may vary based on the type of MRI device producing the field or the type of MRI procedure being performed. A 1.5 T MRI device, for example, will produce a static magnetic field at about 1.5 Tesla and have a corresponding RF frequency of about 64 MHz while a 3.0 T MRI device will produce a static magnetic field at about 3.0 Tesla and have a corresponding RF frequency of about 128 MHz.

Some or all of the various types of fields produced by MRI device 16 (which are represented by energy field 11) may have undesirable effects on implantable medical system 13. Implantable medical system 13 includes an implantable medical device (IMD) 14 and one or more medical leads 15a,b that extend from the IMD 14 to a target location within patient 12, such as within a heart (not shown) of patient 12. In one example, the RF fields generated during the MRI procedure may induce energy on conventional implantable leads (e.g., in the form of a current), which may be conducted to tissue proximate to an electrode of the leads and cause a rise in temperature of the tissue.

As will be described in detail below, one or both of implantable medical leads 15a,b are designed to reduce the undesirable effects the external fields 11 may have on the implantable medical lead and the implantable medical device. In particular, implantable medical leads 15a,b may include an RF filter near a distal end of medical leads 15a,b that reduces the amount of current induced on medical leads 15a,b by energy field 11 of MRI device 16. The RF filter may be electrically connected in series with an electrical path to an electrode of medical leads 15a,b and designed to attenuate energy at frequencies in the range of the frequency of external field 11. The RF filter reduces the amount of current that flows to an electrode of medical leads 15a,b. In this manner, the RF filter acts as trap filter or a choke filter to reduce the amount of current that flows to the electrode and along the lead in general.

Although described mainly in the context of MRI procedures, the techniques of this disclosure may also allow the patient to undergo other medical procedures that generate external fields (such as high frequency RF signals) that may affect operation of the medical electrical lead, such as electrocautery procedures, diathermy procedures, ablation procedures, electrical therapy procedures, magnetic therapy procedures, or the like. Moreover, the medical electrical leads described in this disclosure may also reduce the effects of high frequency signals encountered in medical and non-medical environments, such in an environment with RFID reading devices including surgeries that utilize RFID tagged instruments, towels, or the like.

Figure 2:
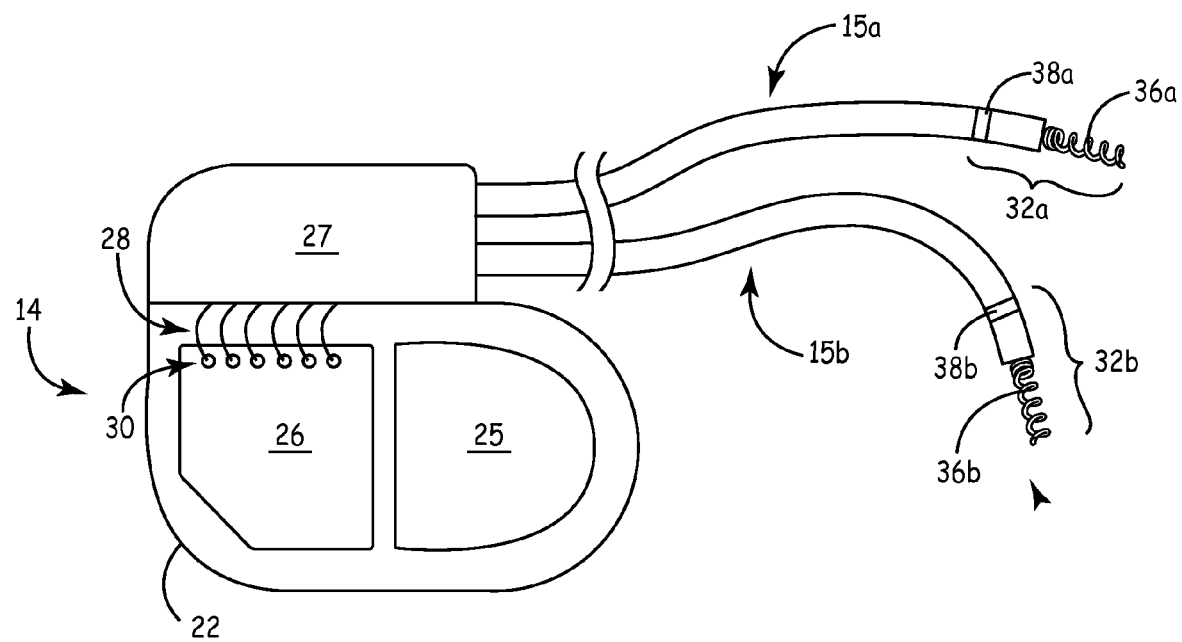
FIG. 2 is a conceptual diagram illustrating an implantable medical system.

FIG. 2 is a conceptual diagram illustrating implantable medical system 13 of FIG. 1 in further detail. Medical system 13 includes IMD 14 and leads 15a, b. IMD 14 may be an implantable cardiac device that senses electrical activity of a heart of patient 12 and/or provides electrical stimulation therapy to the heart of patient 12. IMD 14 may, for example, be an implantable pacemaker, implantable cardioverter defibrillator (ICD), cardiac resynchronization therapy defibrillator (CRT-D), cardioverter device, or combinations thereof. IMD 14 may alternatively be a non-cardiac implantable device, such as an implantable neurostimulator or other device that provides electrical stimulation therapy.

IMD 14 includes a housing 22 within which components of IMD 14 are housed. Housing 22 can be formed from conductive materials, non-conductive materials or a combination thereof. IMD 14 includes a power source 25 and a printed circuit board (PCB) 26 enclosed within housing 22. Power source 25 may include a battery, e.g., a rechargeable or non-rechargeable battery, or other power source. PCB 26 includes one or more electrical components (not shown in FIG. 2) of IMD 14, such as one or more processors, memories, transmitters, receivers, sensors, sensing circuitry, therapy circuitry and other appropriation components. PCB 26 may provide electrical connections between power source 25 and the electrical components of IMD 14 such that power source 25 provides power to the various electrical components of PCB 26. In some examples, PCB 26 may include one or more layers of conductive traces and conductive vias that provide electrical connection between power source 25 and the electrical components as well as provide electrical connections among the various electrical components. PCB 26 may not be limited to typical PCB structures, but may instead represent any structure within IMD 14 that is used to mechanically support and electrically connect the electrical components of IMD 14 and power source 25. Moreover, although the electronics components of IMD 14 are described as being on a single PCB, it is contemplated that the electronic components described herein may be included elsewhere within IMD 14, e.g., on other supporting structures within IMD 14, such as additional PCBs (not shown).

Leads 15a,b include respective electrode assemblies 32a,b located at a distal end of leads 15a,b. In the example illustrated in FIG. 2, electrode assembly 32a,b each include a respective tip electrode 36a,b and ring electrode 38a,b. In other examples, however, electrode assemblies 32a,b may include more or fewer electrodes. As will be described in further detail herein, one or both of electrode assemblies 32a,b include an RF filter (not shown FIG. 2) electrically coupled proximal to electrodes 36a, 36b, 38a or 38b. In one example, the RF filter may comprise a conductor wound in such a manner that the conductor provides an inductance and capacitance that provides the RF filter with a resonant frequency and, in some instances, multiple resonant frequencies. At frequencies around the resonant frequency, the RF filter presents a high impedance, thereby blocking the signal from or at least attenuating the signal propagating to the electrode. At frequencies far from the resonant frequency, the RF filter presents a low impedance. By designing the RF filter to have a resonant frequency around the frequency of MRI device 16, energy induced on leads 15*a,b* by energy field 11 generated by MRI device 16 may be significantly reduced while allowing energy associated with therapies to pass substantially unaffected. In this manner, the RF filter functions as a trap filter or choke filter. In other example, the RF filter may be formed from the wound conductor and one or more other elements, e.g., capacitor or inductor components.

Leads 15*a,b* may also include a fixation mechanism to affix the tip electrodes 36*a,b* and/or ring electrodes 38*a,b* relative to or in a selected tissue, muscle, nerve or other location within the patient 12. The fixation mechanism can be near the tip electrodes 36*a,b* or define a portion of the tip electrodes 36*a,b*. In the example illustrated in FIG. 2, tip electrodes 36*a,b* are formed to define the fixation mechanism. Tip electrodes 36*a,b* take the form of extendable helically shaped electrodes to facilitate fixation of the distal end of electrode assemblies 32*a,b* to patient 12. In other instances, the fixation mechanism may be a separate structure from tip electrode 36*a,b*. Fixation mechanisms can be any appropriate type, including a grapple mechanism, a helical or screw mechanism, a drug-coated connection mechanism in which the drug(s) serves to reduce infection and/or swelling of the tissue, or other attachment mechanism. In addition, the leads 15*a,b* can define an active or passive lead, as discussed herein.

Leads 15*a,b* are connected to IMD 14 via connector block 27. Connector block 27 may include one or more ports that interconnect with one or more connector terminals located on the proximal end of leads 15*a,b*. Leads 15*a,b* are ultimately electrically connected to one or more electrical components on PCB 26 through connecting wires 28, which may extend within connector block 27. For example, connecting wires 28 may be connected to leads 15*ab* at one end, and connected to PCB connection points 30 on PCB 26 at the other end.

One or more conductors (not shown in FIG. 2) can extend within a body of leads 15*a,b* from connector block 27 to engage the ring electrode 38*a,b* and tip electrode 36*a,b*, respectively. The body of leads 15*a,b* may be formed from a non-conductive material, including silicone, polyurethane, fluoropolymers, mixtures thereof, and other appropriate materials, shaped to form a lumen within which the one or more conductors extend. In this manner, each of tip electrodes 36*a,b* and ring electrodes 38*a,b* is electrically coupled to a respective conductor within its associated lead bodies. For example, a first electrical conductor can extend along the length of body of lead 15*a* from connector block 27 and electrically couple to tip electrode 36*a* and a second electrical conductor can extend along the length of the body of lead 15*a* from connector block 27 and electrically couple to ring electrode 38*a*. The respective conductors may couple to circuitry, such as a therapy module or a sensing module, of IMD 14 via connections in connector block 27, connecting wires 28 and PCB connection points 30. The electrical conductors transmit therapy from the therapy module within IMD 14 to one or both of the electrodes and transmit sensed electrical signals from one or both electrodes to the sensing module within IMD 14.

The configuration of implantable medical system 13 illustrated in FIGS. 1 and 2 is merely an example. In other examples, implantable medical system 13 may include more or fewer leads extending from IMD 14. For example, IMD 14 may be coupled to three leads, e.g., a third lead implanted within a left ventricle of the heart of patient 12. In another example, IMD 14 may be coupled to a single lead that is implanted within either an atrium or ventricle of the heart of patient 12. As such, IMD 14 may be used for single chamber or multi-chamber cardiac rhythm management therapy.

In addition to more or fewer leads, each of the leads may include more or fewer electrodes. In instances in which IMD 14 is used for therapy other than pacing, e.g., defibrillation or cardioversion, the leads may include elongated electrodes, which may, in some instances, take the form of a coil. IMD 14 may deliver defibrillation or cardioversion shocks to the heart via any combination of the elongated electrodes and housing electrode. As another example, medical system 13 may include leads with a plurality of ring electrodes, e.g., as used in some implantable neurostimulators, without a tip electrode.

Figure 3:
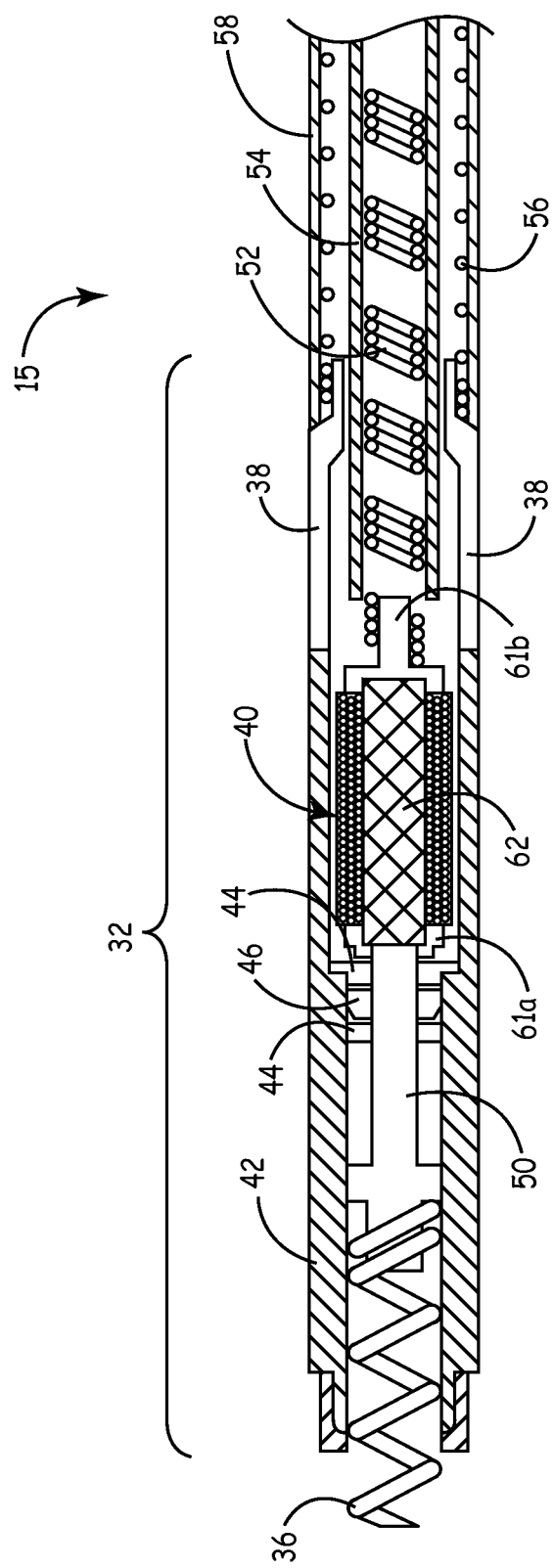
FIG. 3 is a schematic diagram illustrating a longitudinal cross-sectional view of distal end of a lead.

FIG. 3 is a schematic diagram illustrating a longitudinal cross-sectional view of distal end of a lead 15, including electrode assembly 32. Electrode assembly 32 may correspond with electrode assembly 32*a* of lead 15*a* or electrode assembly 32*b* of lead 15*b* of FIG. 2. Electrode assembly 32 includes a tip electrode 36 and a ring electrode 38. However, electrode assembly 32 may include more than two electrodes or only a single electrode. Moreover, tip electrode 36 is illustrated as a helical tip electrode used for fixation. However, tip electrode 36 may not be used for fixation.

Tip electrode 36 is electrically coupled to one or more electronic components of IMD 14 such that an electrical path exists from a proximal end of the lead to tip electrode 36. In the example illustrated in FIG. 3, the electrical path runs from IMD 14 through a tip conductor 52, RF filter 40, conductive electrode shaft 50 to tip electrode 36. Tip conductor 52, RF filter 40, conductive electrode shaft 50 and tip electrode 36, which are all formed at least partially from a conductive material, are mechanically coupled to form the electrical path. RF filter 40 may be formed in accordance with one of the techniques described herein.

Figure 4:
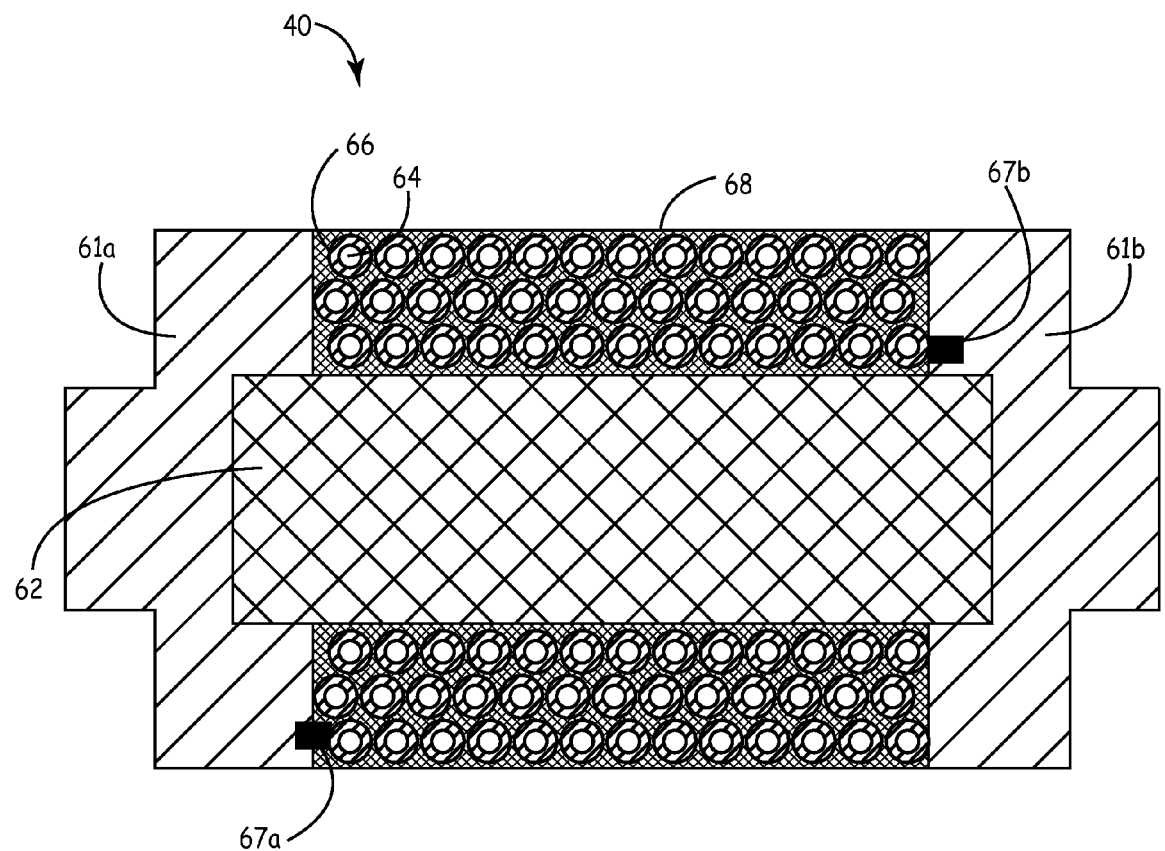
FIG. 4 is a longitudinal cross-sectional view of an example RF filter.

RF filter 40 includes a conductor wound to form RF filter 40. In some instances, the conductor may be wound on a bobbin that may include a cylindrical shaft 62 and at least two electrical transitions or connections. In the example of FIGS. 3 and 4, the electrical transitions are in the form of end caps 61*a*, *b*. In this case, end caps 61*a,b* may be made from a conductive material such that end caps 61*a,b* provide an electrical connection or transition from RF filter 40 to conductive shaft 50 (or directly to electrode 36) and/or to tip conductor 52. RF filter 40 may have electrical transitions or connections that are separate from end caps 61*a,b*. End caps 61*a,b* may, for example, be made from a non-conductive material and one or more electrical connections may be bonded or attached to electrical end caps 61*a,b* to provide the electrical connection of RF filter 40 in series with the electrical path to electrode 36. In further example, RF filter 40 may not include end caps 61*a,b* at all, but instead have a different electrical transition, connection or interconnect mechanism.

In the example of FIG. 3, end cap 61*b* of RF filter 40 is mechanically coupled to tip conductor 52. End cap 61*a* of RF filter 40 is mechanically coupled on conductive electrode shaft 50. End cap 61*a* is also electrically coupled to end cap 61*b* via the wound conductor 69 (illustrated in further detail in FIG. 4). End cap 61*a* may, for example, be mechanically coupled to conductor 69 at the outermost row of windings (e.g., at connection point 67a of FIG. 5) and end cap 61b may be mechanically coupled to conductor 69 at the innermost row of windings (e.g., at connection point 67b of FIG. 5). In another example, end cap 61b may, for example, be mechanically coupled to conductor 69 at the outermost row of windings and end cap 61a may be mechanically coupled to conductor 69 at the innermost row of windings. Tip electrode 36 is mechanically coupled to the opposite end of electrode shaft 50 than end cap 61a. In other instances, RF filter 40 may be directly coupled to an electrode instead of being coupled to electrode shaft 50, as may be the case for other types of distal electrodes, which may take the form of a ring electrode, hemispherical electrode or other type of electrode. The mechanical couplings may be via welding, crimping, soldering or other suitable mechanism.

The mechanical coupling of tip conductor 52, RF filter 40, conductive electrode shaft 50 and tip electrode 36 also provides an electrical path from tip electrode 36 to tip conductor 52 such that electrical signal are conducted from tip electrode 36 to tip conductor 52 through RF filter 40. The mechanical coupling of tip conductor 52, RF filter 40, conductive electrode shaft 50 and tip electrode 36 also provides a mechanical relationship that may, in some instances, allow for mechanical control of tip electrode 36 such that it may be extended from and refracted within a distal end of electrode assembly 32. During implantation, a user may interact with lead 15 to rotate tip conductor 52, which causes RF filter 40 and electrode shaft 50 to rotate and extend tip electrode 36 from the distal end of electrode assembly 32. In this manner, tip electrode 36 may be screwed into the target tissue location within patient 12. In other instances, RF filter 40 or electrode shaft 50 may be formed to receive a stylet to allow a user to extend and/or retract tip electrode 36. For example, RF filter 40 may be formed to provide a lumen through which the stylet, a guidewire, conductors and/or fluid may pass.

Lead 15 also includes a ring conductor 56 located within a body of lead 15 and extending along a length of lead 15 to electrically couple to ring electrode 38. Ring conductor 56 may be comprised of one or more conductive wires each surrounded by a respective insulating jacket. A proximal end of ring electrode 38 may be formed to receive a portion of ring conductor 56. Ring conductor 56 and ring electrode 38 are mechanically coupled (e.g., via welding, soldering, crimping or other mechanism). This provides an electrical path from one or more electrical components of IMD 14 to ring electrode 38. Ring electrode 38 is illustrated in FIG. 3 as having a cylindrical shape, but other shaped electrodes may be utilized in place of a ring electrode. Ring conductor 56 is illustrated in FIG. 3 as having a larger diameter than tip conductor 52. In other instances, tip conductor 52 may have a larger diameter than ring conductor 56 or may have an equal diameter and run the length of the lead body 34 intertwined with ring conductor 56.

At the proximal end of the lead, tip conductor 52 and ring conductor 56 are electrically coupled to one or more electrical components IMD 14, such as an electrical stimulation module or sensing module, via connector block 27. Electrical stimulation may be delivered from IMD 14 to tip electrode 36 and/or ring electrode 38 and sensed electrical signals may be delivered from tip electrode 36 and/or ring electrode 38 via their respective conductors.

Leads 15a,b can be formed to counteract or interact with various environmental factors. For example, the leads 15a,b can include features to block a portion of the energy induced on leads 15a,b by energy field 11 of MRI device 16 or at least attenuate the induced energy on leads 15a,b. As described above, the induced currents can be created due to signals, such as high frequency RF signals, acting on conductors 52, 56 of the leads 15a,b.

As described above, patient 12 which has the implanted medical system 13 may receive a certain therapy or diagnostic technique, such as an MRI procedure that exposes leads 15a,b to high frequency RF pulses and strong magnetic fields to create image data regarding the patient 12. The RF pulses can induce currents within the leads 15a,b of the IMD 14. The current induced in the leads 15a,b can cause certain effects, including heating, of the various lead components and/or tissue near the lead. According to various embodiments, such as those discussed herein, components or mechanisms can be provided to reduce or eliminate the amount of current at the tip electrode 36.

In accordance with the techniques of this disclosure, RF filter 40 is placed in series with the electrical path from tip electrode 36 to the electronic components of IMD 14. RF filter 40 reduces the undesirable effects caused by an external energy source 11, such as the high frequency RF fields generated during an MRI procedure. In one example, RF filter 40 presents a high impedance at frequencies around the resonant frequency of RF filter 40. The resonant frequency of RF filter 40 may be designed to be around the frequency of the RF signals generated by MRI device 16, such as around 64 MHz or 128 MHz for a 1.5 T or 3.0 T MRI device, respectively. However, RF filter 40 may be designed to have a resonant frequency at other frequencies. Thus, RF filter 40 blocks high frequency signals around the resonant frequency from propagating to tip electrode 36 or at least attenuates the high frequency signals around the resonant frequency to reduce the effect at tip electrode 36. At frequencies far from the resonant frequency, RF filter 40 presents a low impedance thereby allowing the low frequency signals, such as those associated with electrical therapies, to pass substantially unaffected. In this manner, RF filter 40 functions as a trap or choke for the RF frequencies associated with MRI device 16. In other examples, RF filter 40 may include one or more other components (such as a capacitor or inductor component(s)) in addition to the wound conductor 69. The other components, e.g., capacitor or inductor, may provide additional capacitance or inductance not realized by the self-capacitance and inductance of wound conductor 69.

Electrode assembly 32 also includes an electrode assembly body 42 that surrounds all, or at least a portion, of tip electrode 36 (depending on whether tip electrode is retracted or not), all or a portion of conductive electrode shaft 50, seal 46, rings 44 and at least a portion of RF filter 40. Electrode assembly body 42 may be of a generally cylindrical shape. Electrode assembly body 42 may be made of a non-conductive material and thus is not electrically conductive. Exemplary material used to form electrode assembly body 42 may include parylene, polyamide, polyimide, metal oxides, urethane, silicone, ethylene tetrafluroethylene (ETFE), polytetrafluroethylene (PTFE), ceramics, or other non-conductive material.

Electrode assembly 32 also includes a seal 46. Seal 46 is in contact with electrode assembly body 42 and electrode shaft 50 to form a seal that prevents fluid from passing into the lumen defined by the body of the lead and housing tip conductor 52, ring conductor 40 and the like. Seal 46 may be substantially ring (e.g. o-ring) or disk shaped but other suitable shapes may also be employed. In one example, seal 46 may be a sealing washer. Seal 46 may be formed from a non-conductive or conductive material or both.

Electrode assembly 32 may also include one more rings 44 that may hold seal 46 in place and/or act as markers to aid in guiding the distal end of the lead to the desired implant location. In some instances, electrode assembly body 42 and/or electrode shaft 50 may also be in contact with rings 44. Rings 44 may, in one example, be shaped as a C-ring to receive seal 46. However, rings of other shapes may be used. Rings 44 may be comprised of a non-conductive material or of a conductive material or both.

Electrode assembly 32 of FIG. 3 is one example of an electrode assembly in accordance with this disclosure. Modifications may be made while still remaining within the scope of this disclosure. For example, instead of a helical tip electrode, tip electrode 36 may take the form of a ring electrode, hemispherical electrode or other electrode. In another embodiment, for example, an RF filter (similar to RF filter 40) may be placed in series with ring electrode 38 to attenuate energy induced by external signal 11 on the conductive path to ring electrode 38.

FIG. 4 is a longitudinal cross-sectional view of RF filter 40. In the example illustrated in FIG. 4, RF filter 40 includes a conductor, such as conductor 69 illustrated and described in more detail with respect to FIG. 5, wound to form RF filter 40. In some instances, conductor 69 may be wound around a bobbin structure that may include a cylindrical shaft 62 and at least two electrical transitions or connections, illustrated as end caps 61*a,b* in FIG. 4. In other instances, RF filter 40 may have electrical transitions or connections that are separate from end caps 61*a,b* and in some instances may not have end caps 61*a,b* at all.

Cylindrical shaft 62 may, in some instances, be formed of any of a variety of non-conductive materials, such as polyether ether ketone (PEEK), polysulphone, ceramic, reinforced polymers, such as polyurethane, or other material. Cylindrical shaft 62 may, in some instances, provide a solid non-conductive core. In other instances, cylindrical shaft 62 may be hollow such that cylindrical shaft 62 forms a lumen through which the stylet, a guidewire, conductors and/or fluid may pass. In some instances, cylindrical shaft 62 may be hollow (e.g., form a lumen) and a solid conductive material may extend through at least a portion of the lumen to provide more structural rigidity. In further instances, cylindrical shaft 62 may function more as a mandrel on which conductor 69 is wound. In this case, cylindrical shaft 62 may be removable such that RF filter 40 has an air core.

End caps 61*a,b* may be formed of any of a variety of conductive materials, such as tantalum, platinum, silver, titanium or any other conductive material, or a combination of conductive materials, including alloys (such as nickel-cobalt-chromium-molybdenum alloy). When end caps 61*a,b* are formed of conductive materials, end caps 61*a,b* provide the electrical transition via which RF filter 40 is electrically coupled in series with the electrical path to tip electrode 36. In other embodiments, end caps 61*a,b* may be formed of a non-conductive material or the bobbin structure may not have end caps 61*a,b*. Instead, other types of electrical transitions or connections may be used electrically connect RF filter 40 in series with the electrical path to tip electrode 36.

RF filter 40 may include a plurality of rows of windings. In the example illustrated in FIG. 4, RF filter 40 includes three rows of windings having substantially the same number of windings and substantially the same spacing between adjacent windings. However, RF filter 40 may include more or fewer rows of windings, e.g., depending on number of windings, wire size, insulation thickness, diameter of windings, dielectric constant of material between the windings/rows, or other factor. In some instances, RF filter 40 may include only a single row of windings. Additionally, the number of windings may vary from row to row. For example, the innermost row may have a larger number of windings than the outermost row. In another example, the outermost row may have a larger number of windings than the innermost row. In further examples, the spacing between adjacent windings may vary from row to row or within a row.

It is desirable that RF filter 40 operate consistently in both a dry environment and a wet environment. When exposed to bodily fluids, the fluids may enter the space between adjacent windings and/or rows of RF filter 40. This may cause a change in the dielectric constant of the material between the windings and/or rows, resulting in a change in the resonance of RF filter 40 and a loss of efficiency. The techniques of this disclosure help mitigate this potential issue by improving the consistency of the dielectric constant wet or dry of the space, if any, between the windings and/or rows of RF filter 40.

As will be described in detail with respect to FIG. 5, conductor 69 forming RF filter 40 may include a conductive core 64, a first insulation layer 66 and a second insulation layer 68. Second insulation layer 68 may have thermal properties (e.g., melting point, glass transition temperature, heat distortion temperature as measured by the ASTM D648 standard) that occur at a lower temperature than the thermal properties of first insulation layer 66. For example, second insulation layer 68 may have a melting point or a heat distortion temperature that is lower than a corresponding melting point or heat distortion temperature of first insulation layer 66, e.g., measured using the same testing standard. In another example, second insulation layer 68 may have a melting point that is lower than a heat distortion temperature of first insulation layer 66.

In some instances, second insulation layer 68 may be formed from a material that is softer (e.g., lower modulus or durometer) than first insulation layer 66. For example, first insulation layer 66 may have a flexural modulus that is at least 100 times and, in some instances, at least 1,000 times the flexural modulus of second insulation layer 68 as measured by the ASTM D790 or ISO 178 testing method. Additionally, the material used as second insulation layer 68 may have a stable dielectric constant over time in both wet and dry environments. For example, the dielectric constant of the second insulation layer 68 may have a maximum dielectric change/stability of ±20% with extended exposure to moisture, such as body fluid or saline. Factors that may influence the dielectric stability include the water vapor transmission rate and/or the water absorption rate of first insulation layer 66 and second insulation layer 68. In one embodiment, second insulation layer 68 may have a water vapor transmission rate that is several orders of magnitude smaller than the water vapor transmission rate of first insulation layer 66, e.g., at least three orders of magnitude and in some instances up to at least five orders of magnitude smaller as measured by the ASTM D570-81 testing standard. In another embodiment, the water absorption rate of second insulation layer 68 may be at least one order of magnitude smaller and in some cases at least two orders of magnitude smaller than the water absorption rate of first insulation material 66 as measured by the ASTM E96 testing standard.

RF filter 40 or a portion of RF filter 40 may be heated to bond second insulation layers 68 of adjacent windings of conductor 69 together in the portion of RF filter 40. The heat may, increase a temperature of the portion of RF filter 40 to a temperature at which second insulation layers 68 become more amenable to bonding with adjacent insulation layers 68. For example, the portion of RF filter 40 may be heated to a temperature at least at or above the heat distortion temperature and, in some instances, closer to a melting point or even above the melting point of second insulation layer 68. At such temperatures, second insulation layer 68 melts, softens (e.g., becomes rubber-like) or otherwise changes state to make it more amenable to bonding with adjacent layers 68. The portion of RF filter 40, however, remains at a temperature below the melting point and/or the heat distortion temperature of first insulation layer 66 such that first insulations layer 66 does not change state. In this manner, second insulation layer 68 of adjacent coils are reflowed and/or bonded with one another via the increase in temperature or the increase in temperature in conjunction with an applied pressure and/or time while first insulation layer 66 remains substantially unchanged.

In the example illustrated in FIG. 4, second insulation layers 68 of adjacent windings of conductor 69 may bond throughout the entire RF filter 40. Reflowing second insulation layer 68 may reduce the amount of space between adjacent windings and/or between the rows of windings, thus reducing the overall size of RF filter 40. In some instances, space between some adjacent windings or rows is eliminated. This improves the resilience of RF filter 40 when implanted within bodily fluid of patient 12. Additionally, the reflowed insulation layer 68 embeds the windings so that the windings, particularly at the ends of RF filter 40 connected to conductive portions 61a,b of the bobbin structure maintain a geometry of RF filter 40 and do not spring back or unwind.

In other instances, second insulation layers 68 of adjacent windings of conductor 69 may bond throughout only a portion of RF filter 40, such as throughout only an outermost portion of RF filter 40 or only at the ends where the conductor is connected to end caps 61a,b. Although second insulation layer 68 is not reflowed throughout the entire RF filter 40, second insulation layer 68 may still provide several benefits. For example, second insulation layer 68 reduces direct contact of first insulation layers 66 of adjacent turns during winding operation. In this manner, second insulation layer 68 protects first insulation layer 66 from damage that may occur during winding of conductor 69. Additionally, second insulation layer 68 protects first insulation layer 66 from high contact pressures between adjacent windings, which may occur as a function of conductor 69 being wound back over itself. In other words, second insulation layer 68 provides protection both between adjacent windings and between rows of windings.

RF filter 40 of FIG. 3 is one example of an RF filter in accordance with this disclosure. Modifications may be made while still remaining within the scope of this disclosure. As indicated above, RF filter 40 may include a different number of rows of windings, different number of windings, different wire sizes, different insulation thicknesses, different diameters of windings, or different dielectric constants of material between the windings/rows depending on the implementation. For example, the number of windings may vary from row to row and/or the spacing between adjacent windings may vary from row to row or within a row.

Figure 5:
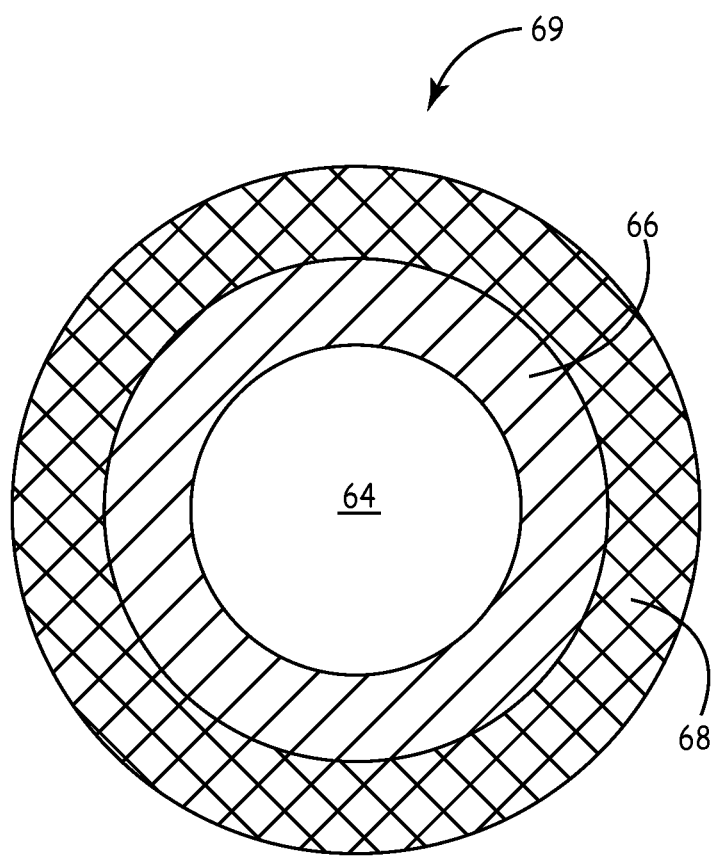
FIG. 5 is a schematic diagram illustrating a cross-sectional view of an example conductor that may be used to form an RF filter.

FIG. 5 is a schematic diagram illustrating a cross-sectional view of an example conductor 69 that may be used to form RF filter 40 of RF filter 40. Conductor 69 includes a conductive core 64, a first insulation layer 66 surrounding conductive core 64, and a second insulation layer 68 surrounding first insulation layer 66. As described above, second insulation layer 68 may have thermal properties (e.g., melting point, heat distortion temperature or glass transition temperature) that occur at a lower temperature than the thermal properties of first insulation layer 66. In some instances, the temperature associated with one or more of the thermal properties of second insulation layer 68 may be at least fifty degrees Celsius and, in some instances, at least one hundred degrees Celsius lower than the temperature associated with the corresponding thermal properties of first insulation layer 66, e.g., measured using the same testing standard. In some instances, second insulation layer 68 may be formed from a material that is softer (e.g., lower flexural modulus as measured by the ASTM D790 standard or durometer as measured by one of the scales of the ASTM D2240 standard) than first insulation layer 66. Additionally, the material used as second insulation layer 68 may have a stable dielectric constant over time in both wet and dry environments. For example, the dielectric constant of the second insulation layer 68 may have a maximum dielectric change/stability of ±20% with extended exposure to moisture, such as body fluid or saline.

Conductive core 64 may include one or more conductive filars. In the example illustrated in FIG. 5, conductive core 64 is a solid core conductor. However, in other examples, conductive core may include a plurality of conductive filars that together form conductive core 64. Conductive core 64 or the conductive filars forming conductive core 64 may be made from any of a variety of conductive materials, such as tantalum, platinum, silver, or any other conductive material, or a combination of conductive materials, including alloys (such as nickel-cobalt-chromium-molybdenum alloy).

First insulation layer 66 surrounding conductive core 64 may be made from any of a number of non-conductive materials, such as soluble imide (SI), parylene, tantalum pentoxide, PTFE, PEEK, liquid crystal polymer (LCP), or other non-conductive material or combination of non-conductive materials. A thickness of first insulation layer 66 may be dependent on a number of factors, including the type of material used, a desired flexibility, a desired rigidity, a desired reliability, desired dielectric strength or other factor. When first insulation layer 66 is made from SI, for example, first insulation layer 66 may have a thickness of approximately 0.0002-0.0006 inches. However, the thickness of first insulation layer 66 may be larger or smaller.

Second insulation layer 68 may be made from any of a number of non-conductive materials, such as ETFE, PTFE, perfluoroalkoxy (PFA), fluorinated ethylene propylene (FEP), urethanes, or other non-conductive material or combination of non-conductive materials. The material selected as second insulation layer 68 may, in part, depend on the material selected for first insulation layer 66 since second insulation layer 68 should have a melting point that is lower than a melting point of first insulation layer 66, e.g., measured using the same testing standard. A thickness of second insulation layer 68 may be dependent on a number of factors, including the type of material used, a desired flexibility, a desired rigidity, a desired reliability or other factor. When second insulation layer 68 is made from ETFE, for example, second insulation layer 68 may have a thickness of approximately 0.0004-0.0008 inches. However, the thickness of second insulation layer 68 may be larger or smaller.

Figure 6:
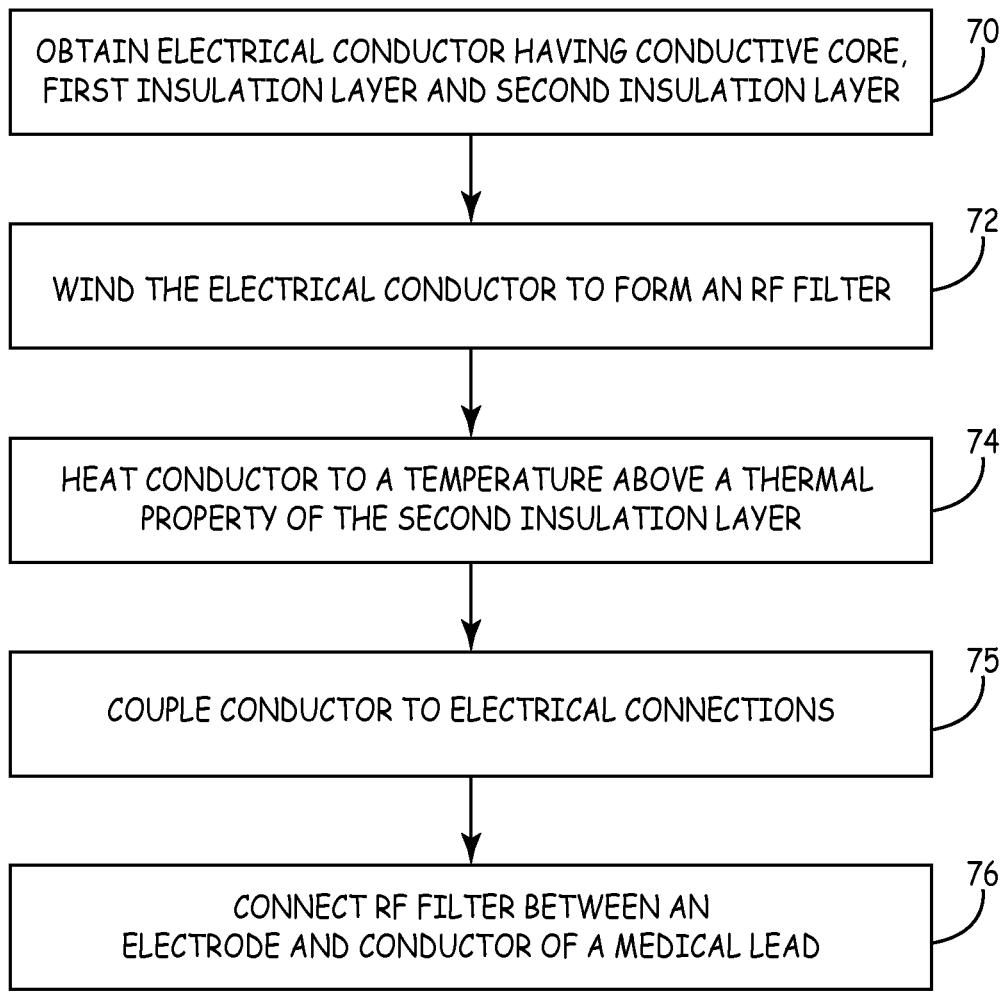
FIG. 6 is a flow diagram illustrating an example method of manufacturing an RF filter.

FIG. 6 is a flow diagram illustrating an example method of manufacturing an RF filter, such as RF filter 40 of FIGS. 3 and 4. An electrical conductor 69 is obtained having a conductive core 64, a first insulation layer 66 surrounding conductive core 64, and a second insulation layer 68 surrounding first insulation layer 66 (block 70). In some instances, second insulation layer 68 may have thermal properties (e.g., melting point, glass transition temperature, heat distortion temperature) that occur at a lower temperature than the thermal properties of first insulation layer 66. In other instances, second insulation layer 68 may be formed from a material that is softer (e.g., lower modulus or durometer) than first insulation layer 66. Additionally, the material used as second insulation layer 68 may have a stable dielectric constant over time in both wet and dry environments.

Electrical conductor 69 is wound to form an RF filter 40 (block 72). As described herein, electrical conductor 69 may be wound around a bobbin structure to form one or more rows of windings of RF filter 40. The number of turns per row and the number of rows may be determined size of conductor 69, thicknesses of insulation layers 66, 68, diameters of the windings, dielectric constants of materials of insulation layers 66, 68, or the like. Additionally, the number of windings may vary from row to row and/or the spacing between adjacent windings may vary from row to row or within a row.

Heat is applied to at least a portion of RF filter 40 to heat the conductor 69 of the portion of RF filter 40 to a temperature at or above at least one of the thermal properties (e.g., melting point, heat distortion temperature or glass transition temperature) of second insulation layer 68, but below any of the thermal properties (e.g., melting point, heat distortion temperature or glass transition temperature) of first insulation layer 66 (block 74). For example, at least a portion of RF filter 40 may be heated to a temperature at or above the melting point or heat distortion temperature of second insulation layer 68 such that second insulation layer 68 melts, softens (e.g., becomes rubber-like) or otherwise changes state to make it more amenable to bonding with adjacent layers 68. The portion of RF filter 40, however, remains at a temperature below the thermal property of first insulation layer 66 such that first insulations layer 66 does not melt or become rubber-like. In this manner, second insulation layers 68 of adjacent coils are reflowed and/or bonded with one another via the increase in temperature without substantially affecting first insulation layer 66. In some instances, pressure may also be applied to assist with the bonding of second insulation layers 68 of adjacent coils. The heat may be applied using a heat gun, a reflow oven, resistance heating by running a current through conductor 69, direct contact heating or other technique. In one embodiment, the bond is achieved because second insulation layers 68 of adjacent windings of conductor 69 reflow to combine with one another.

In some instances, the heat may cause second insulation layer 68 to reflow and bond throughout substantially all of the rows of windings of RF filter 40. For example, the heat may be hot enough or applied long enough to heat second insulation layer 68 of the windings of all of the rows of RF filter 40 to reflow and bond to one another. In another example, the heat may be applied concurrently with the winding of conductor 69 such that the second insulation layer 68 reflows and bonds throughout substantially all of rows of windings of RF filter 40. In this example, the winding and reflowing occurs concurrently. In a further example, the heat may be applied to conductor 69 after each of layers is wound, which may cause the second insulation layer 68 to reflow throughout substantially all of RF filter 40.

In other instances, second insulation layer 68 may be reflowed throughout only a portion of RF filter 40. For example, the heat may be applied after winding all the rows of RF filter 40 to cause second insulation layer 68 of the windings of only an outermost row of RF filter 40 to heat to a temperature at which second insulation layer 68 of those windings reflow and bond to one another. In another example, the heat may be applied to reflow and bond second insulation layer 60 near the ends where conductor 69 is mechanically coupled to end caps 61*a,b*. Although second insulation layer 68 is not reflowed throughout the entire RF filter 40, second insulation layer 68 may provide additional benefits. For example, second insulation layer 68 reduces direct contact of first insulation layer 66 during winding operation. In this manner, second insulation layer 68 protects first insulation layer 66 from damage that may occur during winding of conductor 69. Additionally, second insulation layer 68 protects first insulation layer 66 from high contact pressures between adjacent windings, which may occur as a function of conductor 69 being wound back over itself. In other words, second insulation layer 68 provides protection both between adjacent windings and between rows of windings.

Conductor 69 is coupled to electrical connections of the bobbin structure, such as end caps 61*a,b* of RF filter 40 of FIG. 4 (75). To this end, first insulation layer 66 and second insulation layer 68 may be removed at locations adjacent to conductive end portions 61*a,b* of the bobbin structure to expose conductive core 64. Conductive core 64 of conductor 69 may be mechanically and electrically connected to the respective conductive end portions 61*a,b* to provide a conductive path through RF filter 40. First insulation layer 66 and second insulation layer 68 may be removed via any of a number of techniques including thermal thermal laser ablation, chemical and/or abrasive removal or other technique. First insulation layer 66 and second insulation layer 68 may be removed at selected locations prior to winding, during winding or after the winding.

RF filter 40 may be connected between an electrode 36 and conductor 52 of medical lead 15, as illustrated in FIG. 3 (block 76). Conductive end portion 61*a* may be mechanically coupled to electrode shaft 50 and conductive end portion 61*b* may be mechanically coupled to conductor 52 to place RF filter 40 in-series with the electrical path to tip electrode 36.

Figure 7:
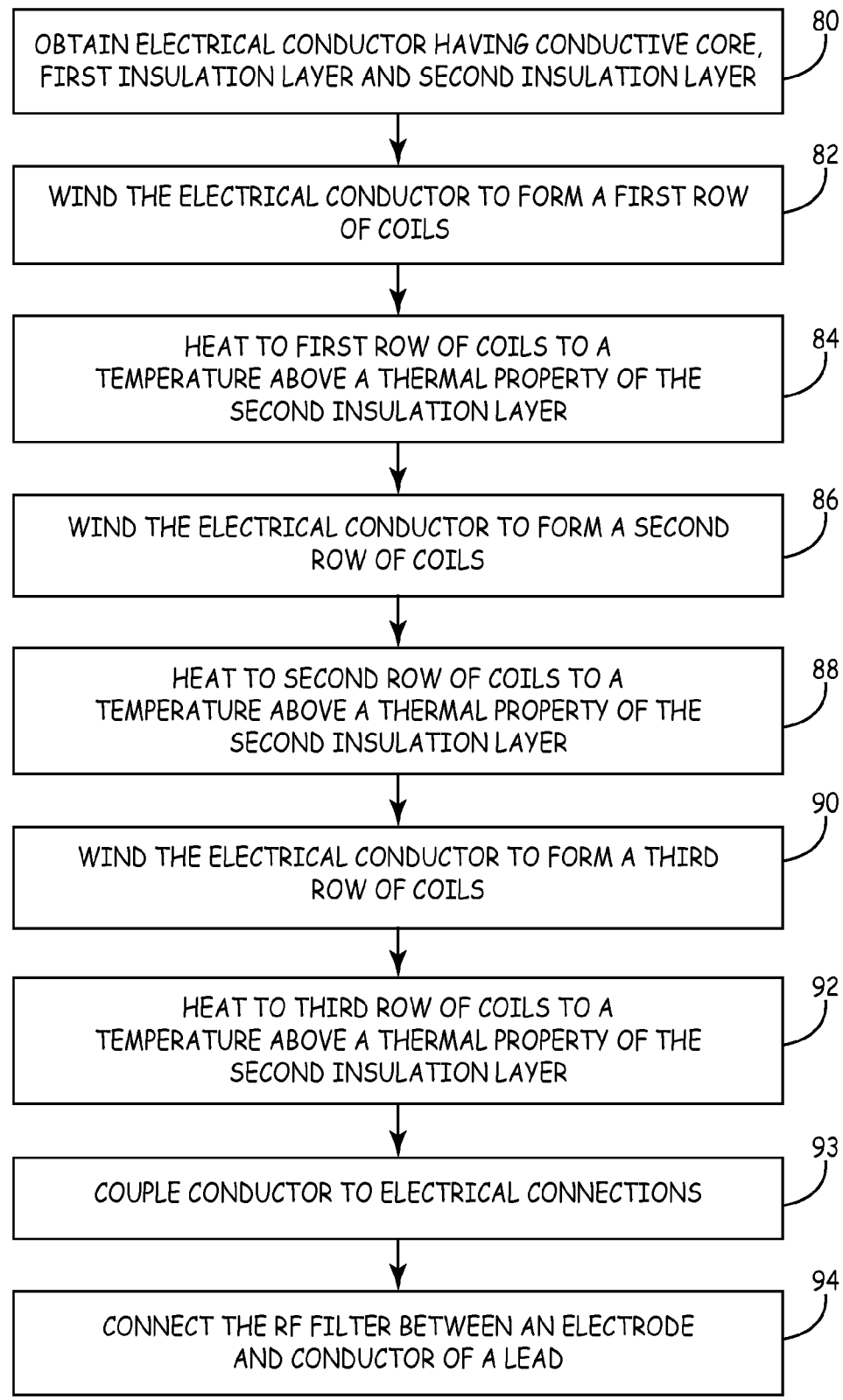
FIG. 7 is a flow diagram illustrating another example method of manufacturing an RF filter.

FIG. 7 is a flow diagram illustrating another example method of manufacturing an RF filter, such as RF filter 40 of FIGS. 3 and 4. An electrical conductor 69 is obtained having a conductive core 64, a first insulation layer 66 surrounding conductive core 64, and a second insulation layer 68 surrounding first insulation layer 66 (block 80). In some instances, second insulation layer 68 may have thermal properties (e.g., melting point, glass transition temperature, heat distortion temperature) that occur at a lower temperature than the thermal properties of first insulation layer 66. In other instances, second insulation layer 68 may be formed from a material that is softer (e.g., lower modulus or durometer) than first insulation layer 66. Additionally, the material used as second insulation layer 68 may have a stable dielectric constant over time in both wet and dry environments.

Electrical conductor 69 is wound to form a first row of windings (block 82). As described herein, electrical conductor 69 may be wound around a cylindrical shaft 62 of a bobbin structure from end cap 61*b* of the bobbin structure to end cap 61*a* of the bobbin structure. Heat is applied to the first row of windings to heat the conductor 69 to a temperature at or above at least one of the thermal properties (e.g., melting point, heat distortion temperature or glass transition temperature) of second insulation layer 68, but below any of the thermal properties (e.g., melting point, heat distortion temperature or glass transition temperature) of first insulation layer 66 (block 84). For example, at least a portion of RF filter 40 may be heated to a temperature at or above the melting point or heat distortion temperature of second insulation layer 68 such that second insulation layer 68 melts, becomes rubber-like or otherwise changes state to make it more amenable to bonding with adjacent layers 68. The portion of RF filter 40, however, remains at a temperature below the thermal property of first insulation layer 66 such that first insulations layer 66 does not melt or become rubber-like. In this manner, second insulation layers 68 of adjacent coils are reflowed and/or bonded with one another via the increase in temperature without substantially affecting first insulation layer 66. In some instances, pressure may also be applied to assist with the bonding of second insulation layers 68 of adjacent coils. The heat may cause second insulation layer 68 of the windings of the first row to reflow and bond throughout at least a portion of the first row and, in some instances, throughout the entire first row.

Electrical conductor 69 is wound to form a second row of windings (block 86). The heat is removed prior to winding the second row of windings. The second row of windings may be wound over the first row of windings from end cap 61*a* of the bobbin structure to end cap 61*a* of the bobbin structure. Heat is applied to the second row of windings to heat the conductor 69 to a temperature at or above at least one of the thermal properties (e.g., melting point, heat distortion temperature or glass transition temperature) of second insulation layer 68, but below any of the thermal properties (e.g., melting point, heat distortion temperature or glass transition temperature) of first insulation layer 66 (block 88). For example, at least a portion of RF filter 40 may be heated to a temperature at or above the melting point or heat distortion temperature of second insulation layer 68 such that second insulation layer 68 melts, becomes rubber-like or otherwise changes state to make it more amenable to bonding with adjacent layers 68. The portion of RF filter 40, however, remains at a temperature below the thermal property of first insulation layer 66 such that first insulations layer 66 does not melt or become rubber-like. In this manner, second insulation layers 68 of adjacent coils are reflowed and/or bonded with one another via the increase in temperature without substantially affecting first insulation layer 66. In some instances, pressure may also be applied to assist with the bonding of second insulation layers 68 of adjacent coils. The heat may cause second insulation layer 68 of the windings of the second row to reflow and bond with adjacent windings throughout at least a portion of the second row of windings and, in some instances, throughout the entire second row of windings. The heat may also cause second insulation layer 68 of the windings of the second row to bond with second insulation layer 68 of the windings of the first row.

Electrical conductor 69 is wound to form a third row of windings (block 90). The heat is removed prior to winding the third row of windings. The third row of windings may be wound over the second row of windings from end cap 61*b* of the bobbin structure to end cap 61*a* of the bobbin structure. Heat is applied to the third row of windings to heat the conductor 69 to a temperature at or above at least one of the thermal properties (e.g., melting point, heat distortion temperature or glass transition temperature) of second insulation layer 68, but below any of the thermal properties (e.g., melting point, heat distortion temperature or glass transition temperature) of first insulation layer 66 (block 92). For example, at least a portion of RF filter 40 may be heated to a temperature at or above the melting point or heat distortion temperature of second insulation layer 68 such that second insulation layer 68 melts, becomes rubber-like or otherwise changes state to make it more amenable to bonding with adjacent layers 68. The portion of RF filter 40, however, remains at a temperature below the thermal property of first insulation layer 66 such that first insulations layer 66 does not melt or become rubber-like. In this manner, second insulation layers 68 of adjacent coils are reflowed and/or bonded with one another via the increase in temperature without substantially affecting first insulation layer 66. In some instances, pressure may also be applied to assist with the bonding of second insulation layers 68 of adjacent coils. The heat may cause second insulation layer 68 of the windings of the third row to reflow and bond with adjacent windings throughout at least a portion of the third row of windings and, in some instances, throughout the entire third row of windings. The heat may also cause second insulation layer 68 of the windings of the third row to combine with second insulation layer 68 of the windings of the second row.

Conductor 69 is coupled to electrical connections of the bobbin structure, such as end caps 61*a,b* of RF filter 40 of FIG. 4 (block 93). To this end, first insulation layer 66 and second insulation layer 68 may be removed at locations adjacent to conductive end portions 61*a,b* of the bobbin structure to expose conductive core 64. Conductive core 64 of conductor 69 may be mechanically connected to the respective conductive end portions 61*a,b* to provide a conductive path through RF filter 40 formed by the wound conductor. First insulation layer 66 and second insulation layer 68 may be removed via any of a number of techniques including thermal laser ablation, chemical and/or abrasive removal or other technique. First insulation layer 66 and second insulation layer 68 may be removed at selected locations prior to winding, during winding or after the winding.

RF filter 40 may be connected between an electrode 36 and conductor 52 of medical lead 15, as illustrated in FIG. 3 (block 94). Conductive end portion 61*a* may be mechanically coupled to electrode shaft 50 and conductive end portion 61*b* may be mechanically coupled to conductor 52 to place RF filter 40 in-series with the electrical path to tip electrode 36.

Figure 8:
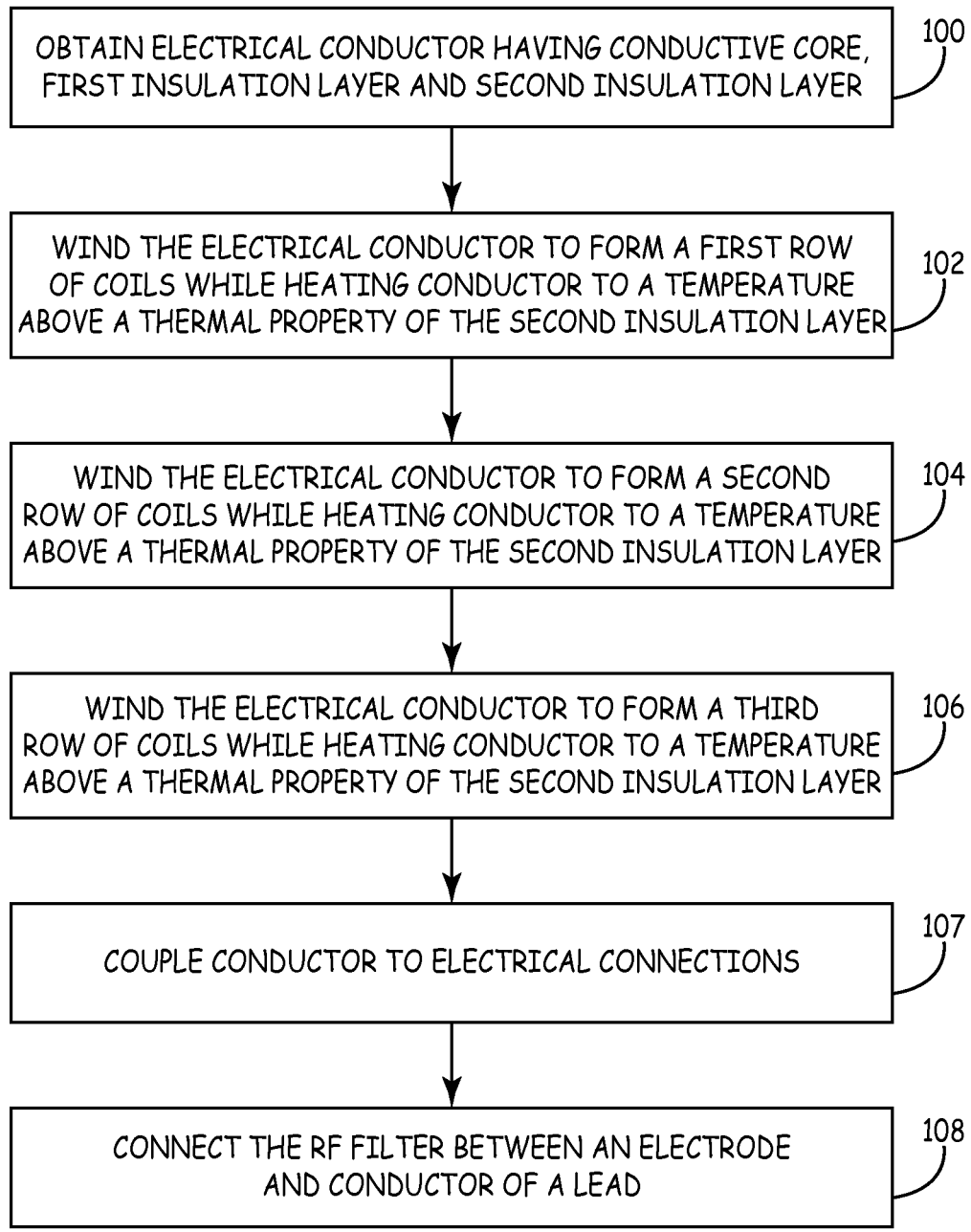
FIG. 8 is a flow diagram illustrating another example method of manufacturing an RF filter.

FIG. 8 is a flow diagram illustrating another example method of manufacturing an RF filter, such as RF filter 40 of FIGS. 3 and 4. An electrical conductor 69 is obtained having a conductive core 64, a first insulation layer 66 surrounding conductive core 64, and a second insulation layer 68 surrounding first insulation layer 66 (block 100). In some instances, second insulation layer 68 may have thermal properties (e.g., melting point, heat distortion temperature, heat distortion temperature) that occur at a lower temperature than the thermal properties of first insulation layer 66. In other instances, second insulation layer 68 may be formed from a material that is softer (e.g., lower modulus or durometer) than first insulation layer 66. Additionally, the material used as second insulation layer 68 may have a stable dielectric constant over time in both wet and dry environments.

Electrical conductor 69 is wound to form a first row of windings while heat is applied to heat the conductor 69 to a temperature at or above at least one of the thermal properties (e.g., melting point, heat distortion temperature or glass transition temperature) of second insulation layer 68, but below any of the thermal properties (e.g., melting point, heat distortion temperature or glass transition temperature) of first insulation layer 66 (block 102). In other words, the heat is applied concurrently with the winding. The heat causes second insulation layer 68 of the windings of the first layer to bond, e.g., by reflowing, throughout at least a portion of the first row of windings and, in some instances, throughout the entire first row of windings. Electrical conductor 69 is wound to form a second layer of windings while heat is applied to heat the conductor 69 to a temperature at or above at least one of the thermal properties (e.g., melting point, heat distortion temperature or glass transition temperature) of second insulation layer 68, but below any of the thermal properties (e.g., melting point, heat distortion temperature or glass transition temperature) of first insulation layer 66 (block 104). The heat causes second insulation layer 68 of the windings of the second layer to bond, e.g., by reflowing, throughout at least a portion of the second row of windings and, in some instances, to bond with second insulation layer 68 of the windings of the first row of windings. Electrical conductor 69 is wound to form a third layer of windings while heat is applied to heat the conductor 69 to a temperature at or above at least one of the thermal properties (e.g., melting point, heat distortion temperature or glass transition temperature) of second insulation layer 68, but below any of the thermal properties (e.g., melting point, heat distortion temperature or glass transition temperature) of first insulation layer 66 (block 106). The heat causes second insulation layer 68 of the windings of the third row to bond, e.g., by reflowing, throughout at least a portion of the third row of windings and, in some instances, to bond with second insulation layer 68 of the windings of the second row of windings.

Conductor 69 is coupled to electrical connections of the bobbin structure, such as end caps 61*a,b* of RF filter 40 of FIG. 4 (block 107). To this end, first insulation layer 66 and second insulation layer 68 may be removed at locations adjacent to conductive end portions 61*a,b* of the bobbin structure to expose conductive core 64. Conductive core 64 of conductor 69 may be mechanically connected to the respective conductive end portions 61*a,b* to provide a conductive path through RF filter 40 formed by the wound conductor. First insulation layer 66 and second insulation layer 68 may be removed via any of a number of techniques including thermal laser ablation, chemical and/or abrasive removal or other technique. First insulation layer 66 and second insulation layer 68 may be removed at selected locations prior to winding, during winding or after the winding.

RF filter 40 may be connected between an electrode 36 and conductor 52 of medical lead 15, as illustrated in FIG. 3 (block 108). Conductive end portion 61*a* may be mechanically coupled to electrode shaft 50 and conductive end portion 61*b* may be mechanically coupled to conductor 52 to place RF filter 40 in-series with the electrical path to tip electrode 36.

FIGS. 6-8 describe example manufacturing processes. One of ordinary skill in the art appreciates that these manufacturing methods may be modified without departing from the scope of this disclosure. For example, each of FIGS. 6-8 is described in the context of an RF filter having three rows of windings. However, the RF filter may have more or fewer rows of windings, e.g., 5 or 7. Moreover, an RF filter may be manufactured with a method that combines aspects from the different methods described above. For example, the conductor may be wound to form a first and second row without applying any heat and then heat may be applied concurrently with winding the third row. Other variations are also within the scope of this disclosure.

Figure 9:
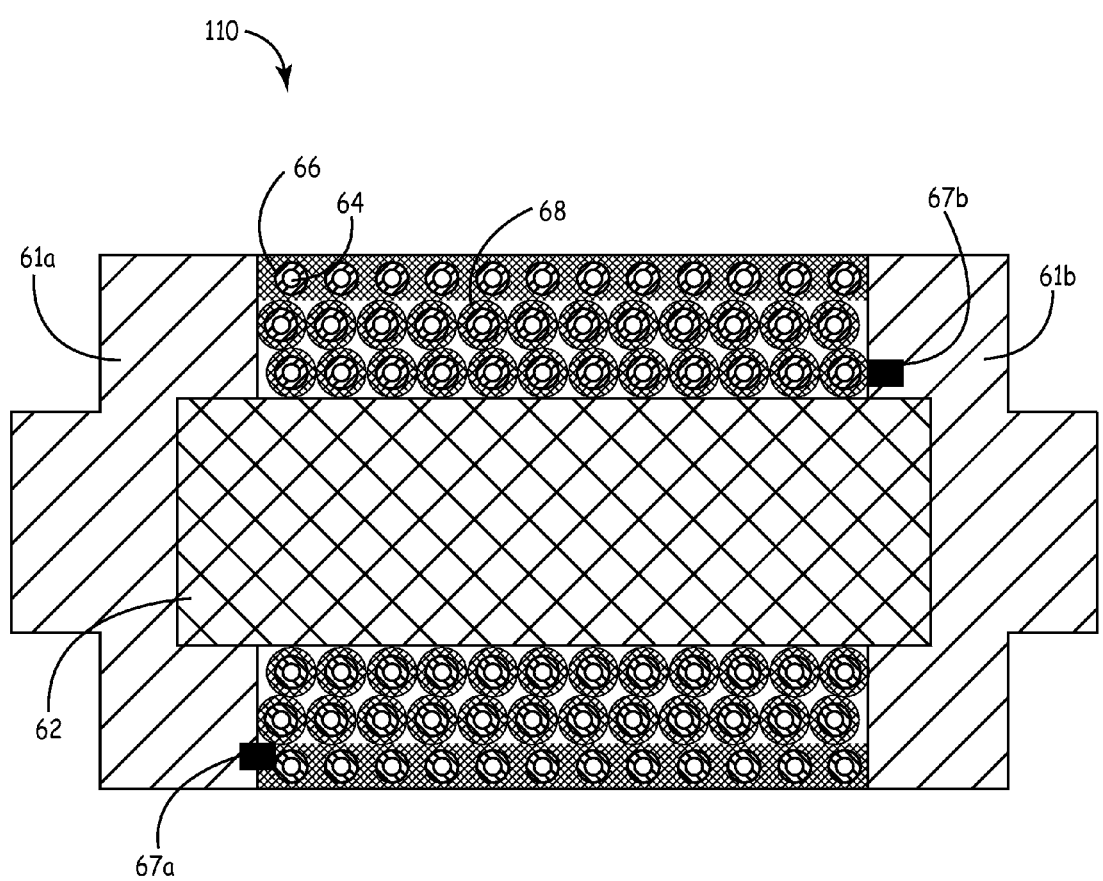
FIG. 9 is a longitudinal cross-sectional view of another example RF filter.

FIG. 9 is a longitudinal cross-sectional view of another example RF filter 110. RF filter 110 of FIG. 9 substantially conforms to RF filter 40 of FIG. 4, but second insulation layer 68 is not reflowed or bonded throughout all of RF filter 110. In the example illustrated in FIG. 9, second insulation layers 68 of the first (innermost row) and the middle row are not reflowed or bonded. However, they may still be in contact with one another. In the outermost layer, however, second insulation layers 68 of the outermost row are reflowed to bond with one another throughout at least a portion of the row. In other embodiments, the middle row and outermost row may be reflowed or otherwise bonded while the innermost row is not.

Various embodiments of the disclosure have been described. It is understood that the present disclosure is not limited for use in pacemakers, cardioverters or defibrillators. Other uses of the leads described herein may include uses in patient monitoring devices, or devices that integrate monitoring and stimulation features. Additionally, skilled artisans appreciate that other configurations and/or dimensions may be used for the mechanical and electrical elements described herein. It is also expected that the teachings herein, while described relative to a bipolar lead, can also be applied to a unipolar or multi-polar lead. These and other embodiments are within the scope of the following claims.

The invention claimed is:

1. A method comprising:
    obtaining an electrical conductor having a conductive core, a first insulation layer surrounding the conductive core, and a second insulation layer surrounding the first insulation layer, wherein the second insulation layer has a thermal property that occurs at a lower temperature than the same thermal property of the first insulation layer;
    winding the electrical conductor to form an RF filter having a resonant frequency that presents a high impedance at frequencies of RF signals generated by a magnetic resonance imaging (MRI) device and presents a low impedance at frequencies associated with electrical stimulation therapies, the RF filter having a plurality of rows of windings including an innermost row and an outermost row, each subsequent row of windings from the innermost row to the outermost row being wound over the previously wound row; and
    heating at least a portion of the RF filter to a temperature at or above the thermal property of the second insulation layer and below the thermal property of the first insulation layer such that the second insulation layers of adjacent windings of the electrical conductor bond throughout at least the portion of the RF filter.

2. The method of claim 1, wherein heating at least the portion of the RF filter comprises heating substantially all of the RF filter to the temperature at or above the thermal property of the second insulation layer and below the thermal property of the first insulation layer such that the second insulation layer of adjacent windings of the electrical conductor bond throughout substantially all of the RF filter.

3. The method of claim 1, wherein
    winding the electrical conductor comprises winding the electrical conductor to form an RF filter having a plurality of rows of windings; and
    heating each of the plurality of rows of windings to the temperature at or above the thermal property of the second insulation layer and below the thermal property of the first insulation layer such that the second insulation layer of adjacent windings bond throughout substantially all of the RF filter.

4. The method of claim 3, wherein winding and heating comprises:
    winding the electrical conductor to form a first row of windings;
    heating at least a portion of the first row of windings to the temperature at or above the thermal property of the second insulation layer and below the thermal property of the first insulation layer such that the second insulation layers of adjacent windings of the first row bond throughout at least the portion of the first row of windings;
    removing the heat;
    winding the electrical conductor to form a second row of windings;
    heating at least a portion of the second row of windings to the temperature at or above the thermal property of the second insulation layer and below the thermal property of the first insulation layer such that the second insulation layers of adjacent windings of the second row bond throughout at least the portion of the second row of windings;
    removing the heat;
    winding the electrical conductor to form a third row of windings; and heating at least a portion of the third row of windings to the temperature at or above the thermal property of the second insulation layer and below the thermal property of the first insulation layer such that the second insulation layers of adjacent windings of the third row bond throughout at least the portion of the third row of windings.

5. The method of claim 1, wherein
winding the electrical conductor comprises winding the electrical conductor to form an RF filter having a plurality of rows of windings; and
applying the heat comprises applying the heat to an outermost row of windings such that the second insulation layers of adjacent windings of at least a portion of the outermost row bond.

6. The method of claim 1, wherein obtaining the electrical conductor comprises obtaining an electrical conductor in which the second insulation layer has a modulus that is lower than a modulus of the first insulation layer.

7. The method of claim 1, wherein obtaining the conductor comprising obtaining a conductor having a second insulation layer made of one or more of ethylene tetrafluroethylene (ETFE), polytetrafluroethylene (PTFE), perfluoroalkoxy (PFA), fluorinated ethylene propylene (FEP), urethanes.

8. The method of claim 7, wherein obtaining the conductor comprising obtaining a conductor having a first insulation layer made of one or more of soluble imide (SI), parylene, tantalum pentoxide, polytetrafluroethylene (PTFE), polyether ether ketone (PEEK), liquid crystal polymer (LCP).

9. The method of claim 1, further comprising connecting the RF filter between an electrode of a lead and a conductor of the lead such that the RF filter is in series with an electrical path to the electrode.

10. The method of claim 1, wherein the thermal property comprises at least one of a melting point, a glass transition temperature and a heat distortion temperature.

11. The method of claim 1, wherein heating at least a portion of the RF filter comprises heating at least a portion of the RF filter to a temperature high enough to cause the second insulation layer to change states to make it more amenable to bonding with second insulation layers of adjacent windings and low enough to not cause the first insulation layer to change states.

12. The method of claim 1, wherein heating at least a portion of the RF filter comprises heating at least a portion of the RF filter to a temperature high enough to cause the second insulation layer to change to a liquid state or a rubber-like state.

13. The method of claim 1, wherein winding the electrical conductor and heating the electrical conductor comprises heating and winding the electrical conductor concurrently.

14. The method of claim 1, wherein second insulation layer has a dielectric constant that changes a maximum of twenty percent when exposed to bodily fluid for an extended period of time.

15. A radio frequency (RF) filter comprising:
a first electrical connection;
a second electrical connection; and
a conductor electrically coupled to the first electrical connection and the second electrical connection to provide a conductive path from the first electrical connection through the RF filter to the second electrical connection, the conductor having a conductive core, a first insulation layer surrounding the conductive core, and a second insulation layer surrounding the first insulation layer, wherein the second insulation layer has a thermal property that occurs at a lower temperature than the same thermal property of the first insulation layer;
wherein the conductor is wound to form a plurality of rows of windings and the second insulation layers of at least a portion of adjacent windings of the conductor are reflowed together, and
wherein the electrical conductor is wound to provide the RF filter with a resonant frequency that presents a high impedance at frequencies of RF signals generated by an magnetic resonance imaging (MRI) device and presents a low impedance at frequencies associated with electrical stimulation therapies.

16. The RF filter of claim 15, wherein substantially all of the second insulation layers of adjacent windings of the conductor are reflowed together.

17. The RF filter of claim 15, wherein the second insulation layers of adjacent windings of the conductor are reflowed together throughout at least a portion of the outermost row of windings.

18. The RF filter of claim 15, wherein the second insulation layer of the conductor has a modulus that is lower than a modulus of the first insulation layer.

19. The RF filter of claim 15, wherein
the second insulation layer is made of one or more of ethylene tetrafluroethylene (ETFE), polytetrafluroethylene (PTFE), perfluoroalkoxy (PFA), fluorinated ethylene propylene (FEP), and urethanes; and
the first insulation layer is made of one or more of soluble imide (SI), parylene, tantalum pentoxide, polytetrafluroethylene (PTFE), polyether ether ketone (PEEK), liquid crystal polymer (LCP).

20. The RF filter of claim 15, wherein the thermal property comprises at least one of a melting point, a glass transition temperature and a heat distortion temperature.

21. The RF filter of claim 15, wherein second insulation layer has a dielectric constant that changes a maximum of twenty percent when exposed to bodily fluid for an extended period of time.

22. An implantable medical lead that includes:
at least one electrode;
at least one conductor that conducts electrical signals to and from the electrode; and
an RF filter connected in series between the electrode and the conductor, wherein the RF filter includes a conductor having a conductive core, a first insulation layer surrounding the conductive core, and a second insulation layer surrounding the first insulation layer, wherein the second insulation layer has a thermal property that occurs at a lower temperature than the same thermal property of the first insulation layer;
wherein the conductor is wound to form a plurality of rows of windings and the second insulation layers of at least a portion of adjacent windings of the conductor are reflowed together, and
wherein the RF filter is configured to have a resonant frequency that presents a high impedance at frequencies of RF signals generated by an magnetic resonance imaging (MRI) device and presents a low impedance at frequencies associated with electrical stimulation therapies.

23. The implantable medical lead of claim 22, wherein substantially all of the second insulation layers of adjacent windings of the conductor are reflowed together.

24. The implantable medical lead of claim 22, wherein the second insulation layers of adjacent windings of the conductor are reflowed together throughout at least a portion of the outermost row of windings.

25. The implantable medical lead of claim 22, wherein the second insulation layer of the conductor has a modulus that is lower than a modulus of the first insulation layer.

26. The implantable medical lead of claim 22, wherein
the second insulation layer is made of one or more of ethylene tetrafluroethylene (ETFE), polytetrafluroethylene (PTFE), perfluoroalkoxy (PFA), fluorinated ethylene propylene (FEP), and urethanes; and
the first insulation layer is made of one or more of soluble imide (SI), parylene, tantalum pentoxide, polytetrafluroethylene (PTFE), polyether ether ketone (PEEK), liquid crystal polymer (LCP).

27. The implantable medical lead of claim 22, wherein the thermal property comprises at least one of a melting point, a glass transition temperature and a heat distortion temperature.

28. The implantable medical lead of claim 22, wherein second insulation layer has a dielectric constant that changes a maximum of twenty percent when exposed to bodily fluid for an extended period of time.

\* \* \* \* \*